US012595283B2

(12) United States Patent
Guo et al.

(10) Patent No.: US 12,595,283 B2
(45) Date of Patent: Apr. 7, 2026

(54) POLYPEPTIDE TAG AND APPLICATION THEREOF IN IN VITRO PROTEIN SYNTHESIS

(71) Applicant: KANGMA-HEALTHCODE (SHANGHAI) BIOTECH CO., LTD, Shanghai (CN)

(72) Inventors: Min Guo, Shanghai (CN); Xue Yu, Shanghai (CN)

(73) Assignee: KANGMA-HEALTHCODE (SHANGHAI) BIOTECH CO., LTD, Shanghai (CN)

( * ) Notice: Subject to any disclaimer, the term of this patent is extended or adjusted under 35 U.S.C. 154(b) by 951 days.

(21) Appl. No.: 17/781,022

(22) PCT Filed: Nov. 27, 2020

(86) PCT No.: PCT/CN2020/132391
§ 371 (c)(1),
(2) Date: May 30, 2022

(87) PCT Pub. No.: WO2021/104482
PCT Pub. Date: Jun. 3, 2021

(65) Prior Publication Data
US 2023/0220004 A1     Jul. 13, 2023

(30) Foreign Application Priority Data

Nov. 30, 2019    (CN) .......................... 201911206616.3

(51) Int. Cl.
*C07K 7/06*      (2006.01)
*C12N 15/62*     (2006.01)
*C12N 15/67*     (2006.01)
*C12N 15/81*     (2006.01)

(52) U.S. Cl.
CPC ............... *C07K 7/06* (2013.01); *C12N 15/62* (2013.01); *C12N 15/67* (2013.01); *C12N 15/815* (2013.01)

(58) Field of Classification Search
None
See application file for complete search history.

(56) References Cited

U.S. PATENT DOCUMENTS

2020/0032275 A1     1/2020  Nakano et al.

FOREIGN PATENT DOCUMENTS

| CN | 108535489 A | 9/2018 |
| CN | 110408635 A | 11/2019 |
| CN | 110408636 A | 11/2019 |
| CN | 111484998 A | 8/2020 |
| IN | 109423496 A | 3/2019 |
| KR | 20130128048 A | 11/2013 |
| KR | 102021348 B1 | 9/2019 |
| WO | 2016204198 A1 | 12/2016 |

OTHER PUBLICATIONS

Nguyen et al. (Applied Microbiology and Biotechnology (2019) 103:2205-2216) (Year: 2019).*
Fisher et al. (J Biol Chem. Jul. 26, 1996;271(30):17718-23) (Year: 1996).*
NCBI XP067124023.1, tetraspanin-9-like [*Centruroides vittatus*] (Year: 2024).*
GenBank AAC49378.1, carbonic anhydrase [*Dunaliella salina*] (Year: 1996).*
May 21, 2024 Rejection issued in Japanese Patent Application No. 2022-532165.
Mar. 26, 2024 Extended European Search Report issued in European Patent Application No. 20894880.2.
Nov. 7, 2023 First Office Action issued in Japanese Patent Application No. 2022-532165.
Mar. 21, 2025 the First Office Action issued in Korean Patent Application No. 10-2022-7022341.
International Search Report dated Feb. 25, 2021 Issued in PCT application PCT/CN2020/132391.
Written Opinion of International Searching Authority dated Feb. 25, 2021 Issued in PCT application PCT/CN2020/132391.
Nguyen, T. K. M. et al., "The NT11, a novel fusion tag for enhancing protein expression in *Escherichia coli*" Applied Microbiology and Biotechnology, vol. (103), pp. 2205-2216, Jan. 4, 2019.
Ki, M. R. et al., "Chimeric protein of internally duplicated a-type carbonic anhydrase from *Dunaliella* species for improved expression and C02 sequestration", Process Biochemistry, vol. (51 ), pp. 1222-1229, May 18, 2016.
Katzen, F. et al., "The past, present and future of cell-free protein synthesis", Trends in Biotechnology, vol. (23), pp. 150-156, Mar. 2005.
Gan, R. et al., "A combined cell-free transcription-translation system from *Saccharomyces cerevisiae* for rapid and robust protein synthesis", Biotechnol. J., vol. (9), pp. 641-651, 2014.
Lu Y. "Cell-free synthetic biology: Engineering in an open world", Synthetic and Systems Biotechnology, vol. (2), pp. 23-27, 2017.
Esposito D. et al., "Enhancement of soluble protein expression through the use of fusion tags", Current Opinion in Biotechnology, vol. (17), pp. 353-358, 2006.

(Continued)

*Primary Examiner* — Sergio Coffa

(57)    ABSTRACT

Provided is a polypeptide tag. The amino acid sequence of the polypeptide tag is Xaa1Xaa2Xaa3PHDYN-Xaa4Xaa5Xaa6 (SEQ ID NO: 37), wherein in the formula, Xaa1, Xaa2, Xaa3, Xaa4, Xaa5, and Xaa6 are each independently an amino acid or none. The polypeptide tag is used for labeling a target protein. In a second aspect, provided is a polypeptide fusion protein, comprising the following two structures: (1) any polypeptide tag according to the first aspect, and (2) a target protein connected to the polypeptide tag. Also provided are an in vitro cell-free protein synthesis system and an application thereof in in vitro protein synthesis. By constructing the polypeptide tag and a target protein as a fusion protein, the expression of the labeled target protein can be effectively increased without removing the polypeptide tag.

9 Claims, 4 Drawing Sheets

Specification includes a Sequence Listing.

(56)     References Cited

OTHER PUBLICATIONS

Kapust R. B. et al., "*Escherichia coli* maltose-binding protein is uncommonly effective at promoting the solubility of polypeptides to which it is fused", Protein Science, vol. (8), pp. 1668-1674, 1999.
Liangfan Zhou et al., "TrxA mediating fusion expression of antimicrobial peptide CM4 from multiple joined genes in *Escherichia coli*", Protein Expression and Purification, vol. (64), pp. 225-230, 2009.
Kohl T. et al., "Automated production of recombinant human proteins as resource for proteome research", Proteome Science, vol. (6), 2008, doi:10.1186/1477-5956-6-4.
Hu J. et al., "Chemical cleavage of fusion proteins for high-level production of transmembrane peptides and protein domains containing conserved methionines", Biochimica et Biophysica Acta, vol. (1778), pp. 1060-1066, 2008.
Da Sol Kim et al., "A new prokaryotic expression vector for the expression of antimicrobial peptide abaecin using SUMO fusion tag", BMC Biotechnology, vol. (19), 2019, doi: 10.1186/s12896-019-0506-x.

* cited by examiner

POLYPEPTIDE TAG AND APPLICATION THEREOF IN IN VITRO PROTEIN SYNTHESIS

CROSS-REFERENCE TO RELATED APPLICATIONS

This application is a national stage application of PCT Patent Application No. PCT/CN2020/132391, filed on Nov. 27, 2020, which claims priority to Chinese Patent Application No. 201911206616.3, filed on Nov. 30, 2019, the content of all of which is incorporated herein by reference.

REFERENCE TO SEQUENCE LISTING

The substitute sequence listing is submitted to replace the sequence listing filed on May 30, 2022 as an ASCII formatted text filed via EFS-Web, with a file name of "Substitute_Sequence_Listing_v2_BSHING-22032-US-PT.TXT", a creation date of Nov. 21, 2022, and a size of 9,806 bytes. The substitute sequence Listing filed via EFS-Web is part of the specification and is incorporated in its entirety by reference herein.

FIELD OF THE INVENTION

The present application relates to the technical field of biochemistry, and more particularly, to a polypeptide tag and an application thereof in an in vitro protein synthesis.

BACKGROUND

A protein is an important molecule in a cell and participates in executing almost all functions of the cell. A difference in a sequence and a structure of the protein, has decided a difference in a function thereof (1). In the cell, the protein can catalyze various biochemical reactions by working as an enzyme, can coordinate various activities of an organism by working as a signal molecule, can support a biological morphology, store an energy, transport a molecule, and make the organism move (2). In the field of biomedicine, a protein antibody acting as a targeting drug, is an important means (1, 2) for treating a plurality of diseases including cancer.

Other than an understanding of an intracellular protein synthesis, a protein synthesis may also be performed outside a cell. An in vitro protein synthesis system generally refers to adding an mRNA template or a DNA template, RNA polymerase, amino acids, ATP and a plurality of other components into a lysis system of bacteria, fungi, plant cell or animal cell, to achieve a rapid and efficient translation (3, 4) of an exogenous protein. Comparing with a traditional in vivo recombinant expression system, an in vitro cell-free protein synthesis system has a plurality of advantages, including being able to express a plurality of specific proteins which may be toxic to the cell or contain a non-natural amino acid (such as a D-amino acid), being able to directly take a PCR product as a template to synthesize multiple proteins in parallel at a same time, so as to carry out a high-throughput drug screening and a proteomics research (3, 5).

It has been reported that a fusion protein technology is one of a plurality of commonly used methods to optimize a production process of a recombinant protein, and is able to achieve a purpose of promoting a target protein expression through a fusion tag. For example, researchers have found that, a strategy of using a protein fusion tag, is effective to increase an expression of a target protein and inhibit a formation of an inclusion body (6). In addition, a plurality of tags being able to be widely used for protein fusion further comprise, but are not limited to, an MBP (Maltose Binding Protein) (7), a TrxA (Thioredoxin A) (8), an NUSA (Nitrogen Utilizing Substance A) (9), a GST (Glutathione-S-Transferase) (10), and a SUMO (Small Ubiquitin-like MOdifier) (11). Wherein most tags used for the protein fusion are a polypeptide chain composed of 20-300 amino acids, and a plurality of disadvantages thereof exist, having a chain length too long, a molecular weight too large, and in most cases, the tag has to be removed from the target protein after an expression is completed, so as to prevent the protein from interfering with a structure and a function of the target protein, and lowering a protein synthesis efficiency. Therefore, in order to reduce an influence and an interference on the target protein by the fusion tag being introduced, there is an urgent need in the art to develop a polypeptide tag which has no or little affect on a protein structure and function, and improves a production efficiency of the target protein.

Therefore, the current technology needs to be improved and developed.

BRIEF SUMMARY OF THE DISCLOSURE

According to the above described defects of the protein synthesis in the prior art, the purpose of the present application is providing a polypeptide tag, having a short polypeptide chain, a small molecular weight, no effect on a special structure of a target protein, no need to be excised, being able to simplify a process flow, improve a production efficiency, and lower a cost. Also, in a case of not cutting the polypeptide tag, the target protein with the tag is still able to improve a protein expression effectively.

In order to achieve the above mentioned goals, the technical solution of the present application to solve the technical problems is as follows:

A first aspect of the present application provides a polypeptide tag, an amino acid sequence of the polypeptide tag is as follows:

Xaa1Xaa2Xaa3PHDYNXaa4Xaa5Xaa6 (SEQ ID NO: 37), wherein each of the Xaa1, Xaa2, Xaa3, Xaa4, Xaa5, Xaa6 is an amino acid or none, independent to each other; the peptide tag is applied to label a target protein. Preferably, the polypeptide tag is applied for an in vivo or an in vitro protein expression based on a *Kluyveromyces lactis* yeast.

Preferably, the Xaa1 in the amino acid sequence of the polypeptide tag is V or none.

Preferably, the Xaa2 in the amino acid sequence of the polypeptide tag is S or none.

Preferably, the Xaa3 in the amino acid sequence of the polypeptide tag is E or none.

Preferably, the Xaa4 in the amino acid sequence of the polypeptide tag is Y or none.

Preferably, the Xaa5 in the amino acid sequence of the polypeptide tag is E or G or none.

Preferably, the Xaa6 in the amino acid sequence of the polypeptide tag is P or K or none.

Preferably, each of the Xaa1, Xaa2, Xaa3, Xaa4, Xaa5, and Xaa6 is independent to each other, wherein:

the Xaa1 is V or none;
the Xaa2 is S or none;
the Xaa3 is E or none;
the Xaa4 is Y or none;
the Xaa5 is E or G or none;
the Xaa6 is P or none.

Preferably, each of the Xaa1, Xaa2, Xaa3, Xaa4, Xaa5, and Xaa6 is independent to each other, wherein:

the Xaa1 is V or none;
the Xaa2 is S or none;
the Xaa3 is E or none;
the Xaa4 is Y or none;
the Xaa5 is G or none;
the Xaa6 is K or none.

Preferably, each of the Xaa1, Xaa2, Xaa3, Xaa4, Xaa5, and Xaa6 is independent to each other, wherein:

the Xaa1 is none;
the Xaa2 is S or none;
the Xaa3 is E or none;
the Xaa4 is Y or none;
the Xaa5 is E or G or none;
the Xaa6 is P or K or none.

Preferably, the Xaa1 is none, the Xaa2Xaa3 is SE or none, and more preferably, the Xaa4Xaa5Xaa6 is YEK.

Preferably, the Xaa1 is none, the Xaa4Xaa5 is YE or YG or none, and more preferably, Xaa4Xaa5Xaa6 is YEP or YGK.

Preferably, the Xaa1Xaa2Xaa3 is VSE, and more preferably, the Xaa4Xaa5 is YE or YG, the Xaa6 is none.

Preferably, the Xaa1 Xaa2Xaa3 is VSE, Xaa4 is none, and more preferably, the Xaa5Xaa6 is EP or Gk.

Preferably, at least three of the Xaa1, Xaa2, Xaa3, Xaa4, Xaa5, Xaa6 are not none; more preferably, the Xaa2Xaa3 and Xaa4 are not none, or the Xaa3 and the Xaa4Xaa5 are not none.

Preferably, the amino acid sequence of the polypeptide tag, wherein the Xaa1 is V, the Xaa2 is S, the Xaa3 is E, the Xaa4 is Y, the Xaa5 is E, the Xaa6 is P.

Preferably, the amino acid sequence of the polypeptide tag, wherein the Xaa1 is V, the Xaa2 is S, the Xaa3 is E, the Xaa4 is Y, the Xaa5 is G, the Xaa6 is K.

Preferably, the amino acid sequence of the polypeptide tag, wherein the Xaa1 is none, the Xaa2 is S, the Xaa3 is E, the Xaa4 is Y, the Xaa5 is E, the Xaa6 is K.

Preferably, the amino acid sequence of the polypeptide tag, wherein the Xaa1 is V, the Xaa2 is S, the Xaa3 is E, the Xaa4 is Y, the Xaa5 is E, the Xaa6 is none.

Preferably, the amino acid sequence of the polypeptide tag, wherein the Xaa1 is none, the Xaa2 is none, the Xaa3 is E, the Xaa4 is Y, the Xaa5 is E, the Xaa6 is K.

Preferably, the amino acid sequence of the polypeptide tag, wherein the Xaa1 is V, the Xaa2 is S, the Xaa3 is E, the Xaa4 is Y, the Xaa5 is none, the Xaa6 is none.

Preferably, the amino acid sequence of the polypeptide tag, wherein the Xaa1 is none, the Xaa2 is none, the Xaa3 is none, the Xaa4 is Y, the Xaa5 is E, the Xaa6 is K.

Preferably, the amino acid sequence of the polypeptide tag, wherein the Xaa1 is V, the Xaa2 is S, the Xaa3 is E, the Xaa4 is none, the Xaa5 is none, the Xaa6 is none A second aspect of the present application provides a polypeptide fusion protein, which is a fusion protein formed by labeling a target protein with any one of the polypeptide tags provided in the first aspect of the present application. The polypeptide fusion protein comprises following two structures: (1) any one of the polypeptide tags provided in the first aspect of the present application, and (2) a target protein connected to the polypeptide tag. A structure of the polypeptide fusion protein comprises a target protein and a polypeptide tag applied to labeling the target protein, forming the fusion protein.

Further, a C-terminus of the polypeptide tag connects to an N-terminus of the target protein.

Further, the target protein is one of a fluorescent protein, an enhanced fluorescent protein, a firefly luciferase, or a combination thereof.

A third aspect of the present application provides an in vitro cell-free protein synthesis system, comprising:

(1) a cell extract;
(2) a DNA or an mRNA encoding any one of the polypeptide fusion proteins provided in the second aspect of the present application.

Preferably, the cell extract is a yeast cell extract; more preferably, the cell extract is a *Kluyveromyces lactis* yeast cell extract.

Further, the in vitro cell-free protein synthesis system further comprises one or more of following components: an amino acid mixture, a dNTP, and an RNA polymerase.

Furthermore, the in vitro cell-free protein synthesis system further comprises one or more of following components: a DNA polymerase, an energy supply system, a polyethylene glycol, and an aqueous solvent.

A fourth aspect of the present application provides an application in the in vitro protein synthesis of a coding gene of any one of the polypeptide tags provided by the first aspect of the present application, or a coding gene of any one of the polypeptide fusion proteins provided by the second aspect of the present application, or any one of the cell-free protein synthesis systems provided by the third aspect of the present application. A synthesized protein is an exogenous protein. Preferably, the application is an in vitro protein synthesis based on the *Kluyveromyces lactis* cell extract.

The present application further discloses an application of the polypeptide tag in an intracellular protein synthesis, more preferably, the application of protein synthesis is in a *Kluyveromyces lactis* cell.

The present application achieves a plurality of following beneficial effects: through the polypeptide tag provided by the present application, a plurality of problems in the prior art are overcome, including: the molecular weight of the tag is relatively large, without a removal, a spatial structure and a function of the target protein will be affected; with a removal, a process and a cost will be increased. The polypeptide tag provided by the present application has a short polypeptide chain, a length thereof is no more than eleven amino acids, and a small molecular weight, without affecting the spatial structure and the biological function of the target protein, does not need to be excised. By constructing the polypeptide tag and the target protein into a fusion protein, without excising the polypeptide tag, an expression level of the tagged target protein can still be increased effectively.

DETAILED DESCRIPTION OF EMBODIMENTS

Nouns and Terms

Figure 1:
FIG. 1 illustrates a schematic diagram on a vector structure of a DNA coding sequence of a polypeptide tag disclosed by the present application connecting to a coding sequence of a target protein (taking eGFP as an example), wherein an eGFP is a coding sequence of an enhanced green fluorescent protein, which is merely an example of a target protein, instead of limiting to the eGFP. Wherein the AUG is an initiation codon, and a "-" between the AUG and the coding sequence of the polypeptide tag is a coding sequence of a connection peptide.

A term "polypeptide tag" in the present application is composed of a plurality of amino acids through a plurality of peptide bonds, applied for a protein labeling.

A term "polypeptide fusion protein" in the present application refers to a protein obtained by expressing a polypeptide tag at an N-terminus or a C-terminus of a target protein.

A term "seamless cloning" in the present application: different from a traditional PCR product cloning, an only difference is that an end of a vector and an end of a primer should both have 15-20 homologous bases, thus both ends of a PCR product obtained therefore are carrying 15-20 bases homogeneous to a vector sequence respectively, and complementary pairing into a ring relying on an inter-base action, which can be directly applied to transform a host bacteria without an enzymatic linking, and a linear plasmid or a circular plasmid entering the host bacteria repairs a gap relying on an enzyme system of the host bacteria.

A term "NT tag" in the present application refers to a small molecule peptide composed of a plurality of amino acids or amino acid residues at the N-terminus of a polypeptide or a protein, and a number behind the NT represents a number of the amino acids in the small molecule peptide, such as NT 11 (eleven peptides), NT 8 (octapeptide), and NT 6 (hexapeptide).

A term "eGFP" in the present application refers to an enhanced Green Fluorescent Protein A term "amino acid mixture" in the present application is a mixture consisting of 20 kinds of natural amino acids or other non-natural amino acids.

A term "N-terminus" in the present application is an amino terminal of an amino acid chain of a peptide or a protein.

A term "C-terminus" in the present application is a carboxyl terminal of an amino acid chain of a peptide or a protein.

A term "energy supply system" in the present application refers to a combination of a plurality of substances that release ATP to provide energy for an in vitro protein synthesis by a hydrolysis or an enzymatic hydrolysis.

A term "dNTP" in the present application refers to a mixture comprising adenine trinucleotide (ATP), thymine trinucleotide (TTP), guanine trinucleotide (GTP) and cytosine trinucleotide (CTP).

In order to make the purpose, technical solution and the advantages of the present application clearer and more explicit, further detailed descriptions of the present application are stated hereafter, referencing to the attached drawings 1-4 and some preferred embodiments of the present application. It should be understood that the detailed embodiments of the application described here are used to explain the present application only, instead of limiting the present application. In the embodiments stated hereafter, an experimental reagent used without any description refers to a conventional commercially available source.

Screening a Polypeptide Tag

After a plurality of experimental designs and experimental verifications, a polypeptide beneficial to improve in vitro protein synthesis efficiency is screened out as a tag. An amino acid sequence of the polypeptide tag is as follows:

Xaa1Xaa2Xaa3PHDYNXaa4Xaa5Xaa6 (SEQ ID NO: 37)

wherein each of the Xaa1, Xaa2, Xaa3, Xaa4, Xaa5, Xaa6 is an amino acid or non, independent to each other; the peptide tag is applied to label a target protein.

Preferably, the Xaa1 in the amino acid sequence of the polypeptide tag is V or none.

Preferably, the Xaa2 in the amino acid sequence of the polypeptide tag is S or none.

Preferably, the Xaa3 in the amino acid sequence of the polypeptide tag is E or none.

Preferably, the Xaa4 in the amino acid sequence of the polypeptide tag is Y or none.

Preferably, the Xaa5 in the amino acid sequence of the polypeptide tag is E or G or none.

Preferably, the Xaa6 in the amino acid sequence of the polypeptide tag is P or K or none.

Preferably, each of the Xaa1, Xaa2, Xaa3, Xaa4, Xaa5, and Xaa6 is independent to each other, wherein:

the Xaa1 is V or none;
the Xaa2 is S or none;
the Xaa3 is E or none;
the Xaa4 is Y or none;
the Xaa5 is E or G or none;
the Xaa6 is P or none.

Preferably, each of the Xaa1, Xaa2, Xaa3, Xaa4, Xaa5, and Xaa6 is independent to each other, wherein:

the Xaa1 is V or none;
the Xaa2 is S or none;
the Xaa3 is E or none;
the Xaa4 is Y or none;
the Xaa5 is G or none;
the Xaa6 is K or none.

Preferably, each of the Xaa1, Xaa2, Xaa3, Xaa4, Xaa5, and Xaa6 is independent to each other, wherein:

the Xaa1 is none;
the Xaa2 is S or none;
the Xaa3 is E or none;
the Xaa4 is Y or none;
the Xaa5 is E or G or none;
the Xaa6 is P or K or none.

Preferably, the Xaa1 is none, the Xaa2Xaa3 is SE or none, and more preferably, the Xaa4Xaa5Xaa6 is YEK.

Preferably, the Xaa1 is none, the Xaa4Xaa5 is YE or YG or none, and more preferably, Xaa4Xaa5Xaa6 is YEP or YGK.

Preferably, the Xaa1Xaa2Xaa3 is VSE, and more preferably, the Xaa4Xaa5 is YE or YG, the Xaa6 is none.

Preferably, the Xaa1 Xaa2Xaa3 is VSE, Xaa4 is none, and more preferably, the Xaa5Xaa6 is EP or Gk.

Preferably, at least three of the Xaa1, Xaa2, Xaa3, Xaa4, Xaa5, Xaa6 are not none; more preferably, the Xaa2Xaa3 and Xaa4 are not none, or the Xaa3 and the Xaa4Xaa5 are not none.

Another embodiment, wherein the amino acid sequence of the polypeptide tag, wherein the Xaa1 is V, the Xaa2 is S, the Xaa3 is E, the Xaa4 is Y, the Xaa5 is E, the Xaa6 is P.

Another embodiment, wherein the amino acid sequence of the polypeptide tag, wherein the Xaa1 is V, the Xaa2 is S, the Xaa3 is E, the Xaa4 is Y, the Xaa5 is G, the Xaa6 is K.

Another embodiment, wherein the amino acid sequence of the polypeptide tag, wherein the Xaa1 is none, the Xaa2 is S, the Xaa3 is E, the Xaa4 is Y, the Xaa5 is E, the Xaa6 is K.

Another embodiment, wherein the amino acid sequence of the polypeptide tag, wherein the Xaa1 is V, the Xaa2 is S, the Xaa3 is E, the Xaa4 is Y, the Xaa5 is E, the Xaa6 is none.

Another embodiment, wherein the amino acid sequence of the polypeptide tag, wherein the Xaa1 is none, the Xaa2 is none, the Xaa3 is E, the Xaa4 is Y, the Xaa5 is E, the Xaa6 is K.

Another embodiment, wherein the amino acid sequence of the polypeptide tag, wherein the Xaa1 is V, the Xaa2 is S, the Xaa3 is E, the Xaa4 is Y, the Xaa5 is none, the Xaa6 is none.

Another embodiment, wherein the amino acid sequence of the polypeptide tag, wherein the Xaa1 is none, the Xaa2 is none, the Xaa3 is none, the Xaa4 is Y, the Xaa5 is E, the Xaa6 is K.

Another embodiment, wherein the amino acid sequence of the polypeptide tag, wherein the Xaa1 is V, the Xaa2 is S, the Xaa3 is E, the Xaa4 is none, the Xaa5 is none, the Xaa6 is none Constructing and Identifying a Plasmid of the Polypeptide Fusion Protein by Sequencing Fusing a coding sequence of a polypeptide tag screened out to a position in a coding sequence of a target protein N-terminus of a pD2P plasmid by a seamless cloning method and adopting a pair of primers. A fusion protein expressed in such a way, wherein a C-terminus of the polypeptide tag is linked to an N-terminus of the target protein by a peptide bond. In an embodiment, a gene sequence encoding the polypeptide tag is ligated to the position of the N-terminus gene sequence of the eGFP in a pD2P-eGFP plasmid (a pD2P plasmid having a gene sequence encoding the eGFP inserted). Specifically, a series of plasmids containing a plurality of gene sequences encoding the polypeptide fusion proteins were constructed, such as a plasmid numbered pD2P-1.07-001.

A basic structure of the pD2P plasmid, please refer to accompanying drawings in a description of Chinese patent application document CN 201910460987.8.

Designing A primer pair based on a cloning technology adopted, performing a PCR amplification by taking a series of the plasmids containing the polypeptide fusion proteins stated above as a plurality of templates respectively, and taking 5 μL of an amplified product to perform an identification by 1% agarose electrophoresis; adding 0.5 μL of DpnI into 10 μL of the amplified product, incubating at 37° C. for 6h; add 50 μL of DH5α competent cells into a centrifuge tube containing a DpnI-treated product, mixing gently, and placing on ice for 30 min, before performing a heat shock at 42° C. for 45s, placing on ice immediately for 3 min, adding 700 μL of LB liquid culture medium into the centrifuge tube. Placing and the centrifuge tube on a shaker at 37° C., shaking and culturing for 1 hour, before taking 200 μL of a culture solution and spread on a solid LB culture medium containing 100 mmol/L of ampicillin, and culturing at 37° C. for 14-16h. After that, selecting a white plaque for sequencing, after confirming that gene sequencing is correct, the plasmid is extracted and stored at −20° C.

In Vitro Cell-Free Protein Synthesis System

In an embodiment, an in vitro cell-free protein synthesis reaction system comprises a cell extract and a DNA encoding a polypeptide fusion protein.

In one embodiment, the in vitro cell-free protein synthesis reaction system comprises a cell extract, a DNA encoding the polypeptide fusion protein, and one or more as follows: an amino acid mixture, a dNTP, and an RNA polymerase.

In one embodiment, the in vitro cell-free protein synthesis reaction system comprises a cell extract, a DNA encoding the polypeptide fusion protein, and one or more as follows: an amino acid mixture, a dNTP, an RNA polymerase, a DNA polymerase, an energy supply system, a polyethylene glycol, and an aqueous solvent.

In one embodiment, the in vitro cell-free protein synthesis reaction system is as follows: Tri-hydroxymethylaminomethane (Tris-HCl) with a final concentration of 9.78 mM and pH 8.0, 80 mM potassium acetate, 5.6 mM magnesium ion, 1.5 mM nucleoside triphosphate (dNTP, including adenine nucleoside triphosphate, guanine nucleoside triphosphate, cytosine nucleoside triphosphate, and uracil nucleoside triphosphate, each nucleoside triphosphate having a concentration of 1.5 mM), 0.7 mM amino acid mixtures (glycine, alanine, valine, leucine, isoleucine, phenylalanine, proline, tryptophan, serine, tyrosine, cysteine, methionine, asparagine, glutamine, threonine, aspartic acid, glutamic acid, lysine, arginine and histidine, a concentration respectively is 0.7 mM), 1.7 mM dithiothreitol, polyethylene glycol, an energy supply system, 24 mM tripotassium phosphate, 50% volume of the cell extract, 0.33 μg/μL DNA template.

In one embodiment, the magnesium ion comes from a magnesium salt selected from one or a combination of a group comprising magnesium glutamate or magnesium acetate.

In one embodiment, the amino acid mixture comprises 20 kinds of natural amino acids, as well as one or a plurality of other non-natural amino acids.

In one embodiment, the polyethylene glycol has a molecular weight of 200-12000 Da, preferably 400, 600, 800, 2000, 4000, 8000 Da, counted as a weight average molecular weight.

In one embodiment, the energy supply system is selected from one or a combination in a group comprising: glucose, maltose, trehalose, maltodextrin, starch dextrin, phosphocreatine, and phosphokinase; preferably, 320 mM maltodextrin, 6% trehalose.

In one embodiment, the cell extract is selected from: an eukaryotic cell, a yeast cell, a *Kluyveromyces* yeast cell; and preferably, a lactic *Kluyveromyces* yeast cell. More preferably, a lactic *Kluyveromyces* yeast cell with a T7RNA polymerase integrated into a genome thereof, or a lactic *Kluyveromyces* yeast cell with a plasmid having a T7RNA polymerase inserted.

In another embodiment, the cell extract is selected from a lactic *Kluyveromyces* yeast cell having been artificially cultured for a high protein yield, specifically, a lactic *Kluyveromyces* yeast cell with a genome having a DNA polymerase gene integrated, and more specifically, a lactic *Kluyveromyces* yeast cell with a genome having a phi29 polymerase gene integrated.

In one embodiment, the DNA template is a DNA encoding a polypeptide fusion protein, comprising a polypeptide fusion fluorescent protein, a polypeptide fusion firefly luciferase, and preferably, a DNA encoding a polypeptide fusion enhanced green fluorescent protein (eGFP).

Embodiment 1: Determination of a Sequence of a Polypeptide Tag 1.1 A source and a determination of an amino acid sequence of a polypeptide tag: it has been reported in a published literature that a researcher has confirmed through a plurality of experiments that, first 11 amino acid residues in an N-terminus half domain of a *Dunaliella* carbonic anhydrase (dca) (an amino acid sequence of NT11 is shown in SEQ ID No.: 18; a DNA sequence is shown in SEQ ID No.:9) linking to an N-terminus of an exogenous protein for fusion expression is able to improve a translation level of the protein, such as YFP (yellow fluorescent protein) and more in a BL21 (DE3) *E. coli* cell (Thi Khoa My Nguyen, et al. The NT11, a novel fusion tag for enhancing protein expression in *Escherichia coli.* 2019; 103(5):2205-2216.). The present embodiment screens out an amino acid sequence that is able to significantly improve an expression of an exogenous protein by a plurality of experiments, after a partial site deletion or a random point mutation of the amino acid sequence of NT11.

Specifically, the amino acid sequence of NT11 (PC) is subjected to a step-by-step deletion or a random point mutation to obtain a series of different amino acid sequences, and a plurality of corresponding nucleotide sequences are obtained by a codon optimization, the amino acid and the nucleotide sequence are then numbered, and a partial sequence obtained is shown in Table 1 and SEQ ID No: 1-18 in the sequence listing.

TABLE 1

| Polypeptide tag plasmids and related sequences | | |
|---|---|---|
| Title of polypeptide tag plasmids | Nucleotide sequences encoding polypeptide tags SEQ ID No.: | Amino acid sequence of polypeptide tags SEQ ID No.: |
| pD2P-1.07-001 | 1 | 10 |
| pD2P-1.07-002 | 2 | 11 |
| pD2P-1.07-003 | 3 | 12 |
| pD2P-1.07-004 | 4 | 13 |
| pD2P-1.07-005 | 5 | 14 |
| pD2P-1.07-006 | 6 | 15 |
| pD2P-1.07-007 | 7 | 16 |
| pD2P-1.07-008 | 8 | 17 |
| PC | 9 | 18 |

As a preferred embodiment, the Xaa1 is V, Xaa2 is S, Xaa3 is E, Xaa4 is Y, Xaa5 is E, Xaa6 is P, the nucleotide sequence is as SEQ ID No.:1, and the amino acid sequence is as SEQ ID No.:10.

As another preferred embodiment, the Xaa1 is V, Xaa2 is S, Xaa3 is E, Xaa4 is Y, Xaa5 is G, Xaa6 is K, the nucleotide sequence is as SEQ ID No.:2, and the amino acid sequence is as SEQ ID No.:11.

As another preferred embodiment, the Xaa1 is none, Xaa2 is S, Xaa3 is E, Xaa4 is Y, Xaa5 is E, Xaa6 is K, the nucleotide sequence is as SEQ ID No.:3, and the amino acid sequence is as SEQ ID No.:12.

As another preferred embodiment, the Xaa1 is V, Xaa2 is S, Xaa3 is E, Xaa4 is Y, Xaa5 is E, Xaa6 is none, the nucleotide sequence is as SEQ ID No.:4, and the amino acid sequence is as SEQ ID No.:13.

As another preferred embodiment, the Xaa1 is none, Xaa2 is none, Xaa3 is E, Xaa4 is Y, Xaa5 is E, Xaa6 is K, the nucleotide sequence is as SEQ ID No.:5, and the amino acid sequence is as SEQ ID No.:14.

As another preferred embodiment, the Xaa1 is V, Xaa2 is S, Xaa3 is E, Xaa4 is Y, Xaa5 is none, Xaa6 is none, the nucleotide sequence is as SEQ ID No.:6, and the amino acid sequence is as SEQ ID No.:15.

As another preferred embodiment, the Xaa1 is none, Xaa2 is none, Xaa3 is none, Xaa4 is Y, Xaa5 is E, Xaa6 is K, the nucleotide sequence is as SEQ ID No.:7, and the amino acid sequence is as SEQ ID No.:16.

As another preferred embodiment, the Xaa1 is V, Xaa2 is S, Xaa3 is E, Xaa4 is none, Xaa5 is none, Xaa6 is none, the nucleotide sequence is as SEQ ID No.:8, and the amino acid sequence is as SEQ ID No.:17.

The 8 polypeptide tags newly obtained above are only some of the preferred embodiments provided by the present application, and the embodiments of the present application include, but not limited to, the preferred embodiments mentioned above.

Embodiment 2: Constructing a Plasmid of eGFP with an N-Terminus Fusion Polypeptide Tag Plasmid construction: Fusing a coding sequence of a polypeptide tag to a position in a coding sequence of an N-terminus of eGFP in a pD2P-eGFP plasmid by a seamless cloning method and adopting a pair of primers. A gene structure thereof is shown in FIG. 1. Wherein titles of the 9 plasmids are: pD2P-1.07-(001-008) and PC (shown in Table 1). The sequences of the amplification primers of the 9 plasmids are SEQ ID No.: 19-36.

A specific construction process is as follows:

Designing a pair of primers according to the seamless cloning method (shown in Table 2, wherein a tail conjugate PF is corresponding to a forward primer, a tail conjugate PR is corresponding to a reverse primer, taking the 9 plasmids sated above: the pD2P-1.07-(001-008) and the PC, as templates respectively, and performing a PCR amplification, then taking 5 μL of an amplification product to perform an electrophoresis identification in 1% agarose. Adding 0.5 μL of DpnI into 10 μL of the amplification product, incubating at 37° C. for 6h; adding 50 μL of DH5α competent cells into a centrifuge tube containing the DpnI treated product, mixing gently and placing on ice for 30 min, before performing a heat shock at 42° C. for 45 seconds, placing immediately on ice for 3 minutes, and adding 700 μL of an LB liquid culture medium into the centrifuge tube. Placing the centrifuge tube on a 37° C. shaker, shaking and culturing for 1 h, then coating 200 μL of a culture solution on a solid LB culture medium containing 100 mmol/L ampicillin and culturing at 37° C. for 14-16 h. After the colonies grow up, picking a plurality of white colonies for an identifying, and after confirming a gene sequencing result to be correct, extracting the plasmids corresponding to the colonies and stored at −20° C.

TABLE 2

| PRIMER SEQUENCE | | |
|---|---|---|
| Title of plasmid | Title of primer | SEQ ID NO.: |
| pD2P-1.07-001 | D2P-1.07-001__PF | 19 |
| | D2P-1.07-001__PR | 20 |
| pD2P-1.07-002 | D2P-1.07-002__PF | 21 |
| | D2P-1.07-002__PR | 22 |
| pD2P-1.07-003 | D2P-1.07-003__PF | 23 |
| | D2P-1.07-003__PR | 24 |
| pD2P-1.07-004 | D2P-1.07-004__PF | 25 |
| | D2P-1.07-004__PR | 26 |
| pD2P-1.07-005 | D2P-1.07-005__PF | 27 |
| | D2P-1.07-005__PR | 28 |
| pD2P-1.07-006 | D2P-1.07-006__PF | 29 |
| | D2P-1.07-006__PR | 30 |
| pD2P-1.07-007 | D2P-1.07-007__PF | 31 |
| | D2P-1.07-007__PR | 32 |
| pD2P-1.07-008 | D2P-1.07-008__PF | 33 |
| | D2P-1.07-008__PR | 34 |

TABLE 2-continued

| PRIMER SEQUENCE | | |
| --- | --- | --- |
| Title of plasmid | Title of primer | SEQ ID NO.: |
| PC | PC_PF | 35 |
| | PC_PR | 36 |

Embodiments 3-5: An Application in an In Vitro Protein Synthesis of a Coding Gene of the Polypeptide Tag, a Coding Gene of eGFP with the N-Terminus Having the Polypeptide Tag Fusion, and an In Vitro Cell-Free Protein Synthesis System Containing the Coding Gene Mentioned Above in a DNA Template Thereof S1: DNA amplification: taking a constructed plasmid as a template and performing a DNA amplification, an amplification system is as follows: a random primer having a final concentration of 1-5 μM (NNNNNNN (SEQ ID NO: 38), representing being composed of 7 bases randomly), 1.14 ng/μL of the plasmid template, 0.5-1 mM of dNTP, 0.1 mg/mL of BSA, 0.05-0.1 mg/mL of Phi29DNA polymerase, lx phi29 reaction buffer (comprising 200 mM of Tris-HCl, 20 mM of $MgCl_2$, 10 mM of $(NH_4)_2SO_4$, 10 mM of KCl, pH7.5). After mixing the reaction system uniformly, placing in an environment at 30° C. and reacting for 3 h. After the reaction is finished, a DNA concentration can be determined by using an ultraviolet spectrophotometer.

An experimental group (treatment method): adding a DNA template, the DNA template comprises a nucleotide sequence encoding the enhanced green fluorescent protein eGFP having the polypeptide tag fused.

A BC group (treatment method): BC, that is, a blank control, adding a DNA template, the DNA template comprises a nucleotide sequence encoding an enhanced green fluorescent protein eGFP without encoding a polypeptide tag.

A PC group (treatment method): PC, that is, a positive control, adding a DNA template, the DNA template comprises a nucleotide sequence encoding the nucleotide sequence of the enhanced green fluorescent protein eGFP having a wild-type coding polypeptide tag fused.

An NC group (treatment method): NC, that is, a negative control, having no exogenous DNA template added.

S2: Expression of the eGFP having the polypeptide tag fused on the N-terminus in an in vitro protein synthesis system.

Adding the DNA fragment having been amplified in the S1 to the in vitro protein synthesis system. The in vitro cell-free protein synthesis reaction system is as follows: a final concentration of 9.78 mM of Tris-HCl, with a pH 8.0, 80 mM of potassium acetate, 5.6 mM of magnesium ion, 1.5 mM of a nucleoside triphosphate mixture (adenine nucleoside triphosphate, guanine nucleoside triphosphate, cytosine nucleoside triphosphate, and uracil nucleoside triphosphate, a concentration of each nucleoside triphosphate is 1.5 mM), 0 7 mM of amino acid mixture (glycine, alanine, valine, leucine, isoleucine, phenylalanine, proline, tryptophan, serine, tyrosine, cysteine, methionine, asparagine, glutamine, threonine, aspartic acid, glutamic acid, lysine, arginine and histidine, a concentration is 0.7 mM respectively), 1.7 mM of dithiothreitol, 2% (w/v) polyethylene glycol 8000, 320 mM of maltodextrin, 6% trehalose, 24 mM of tripotassium phosphate, 50% yeast cell extract by volume, 0.33 μg/μL DNA template (obtained by the DNA amplification stated above).

Adopting three different yeast cell extract sources and constructing different in vitro protein synthesis systems respectively, to verify an effect in different systems of the polypeptide fusion protein being constructed. Wherein the cell extract adopted in the Embodiment 3 is YY1904102, the cell extract adopted in the Embodiment 4 is YY1908191, the cell extract adopted in the Embodiment 5 is YY1904224, all belong to *Kluyveromyces lactis* strain ATCC8585 and different strains that have undergone different genetic modification, including a modification of an endogenous expression of a RNA polymerase, referencing to a preparation method of Chinese patent application document CN201710768550.1.

Placing the reaction system stated above under an ambient condition of 30° C., standing and incubating for about 20 hours. After the reaction is finished, placing the reaction system immediately in an Envision 2120 multi-functional ELISA (Perkin Elmer), reading and detecting a Fluorescence signal strength of the eGFP, and a Relative Fluorescence Unit value (RFU) is applied as an active unit.

Experimental Results:

A plurality of measuring results by a fluorescence spectrophotometry have shown that, in the in vitro protein synthesis system, the wild-type peptide tag not only failed to enhance a protein expression, but led to a decrease in the protein expression. Referencing to FIGS. 2-4, the RFU values of the PC group are all lower than that of the BC group, especially in the FIG. 4, an inhibitory effect is very significant. This is totally different to a promoting effect of the wild-type polypeptide tag in *E. coli* cells.

Using the peptide tags being screened out in the present application, all can promote the in vitro expression of eGFP. From the results of fluorescence photometry, it can be seen that, for various eGFP with an N-terminus having polypeptide tags fused expressed in the in vitro protein synthesis system, the RFU values thereof have increased, indicating that the polypeptide tags of the present application have increased the expression of eGFP, referencing to the FIGS. 2-4.

Figure 2:
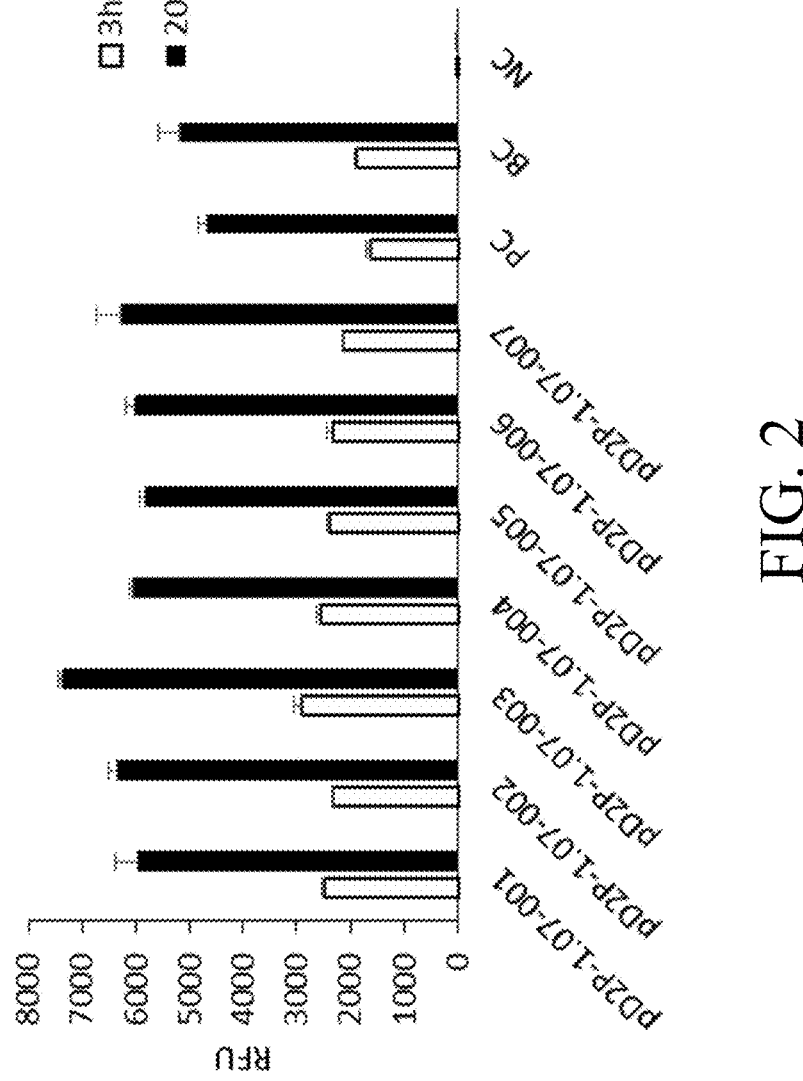
FIGS. 2-4 illustrate a comparison chart on a protein expression effect of various eGFP having the polypeptide tag fused on the N-terminus in different in vitro cell-free protein synthesis system respectively. Wherein, BC (Blank Control) is a blank control of the eGFP with the N-terminus having no sequence on the polypeptide tag fused, and PC (Positive Control) is a positive control of the eGFP with the N-terminus having a sequence on a wild-type polypeptide tag fused, and NC (Negative Control) is a negative control of a DNA template without a coding protein added. Wherein, a cell extract used in the FIG. 2 is YY1904102, a cell extract used in FIG. 3 is YY1908191, a cell extract used in FIG. 4 is YY1904224, all of the cell extracts are different strains of the *Kluyveromyces lactis* yeast after being genetically modified, including a modification of an endogenous expression of the RNA polymerase.

For Embodiment 3, a result thereof is referencing to the FIG. 2, the different experimental groups have all exceeded the blank control group, especially for pD2P-1.07-003 (the RFU value was as high as 7361 after 20 hours), comparing to the blank control having no polypeptide tag related sequences inserted (the RFU value is 5189). the RFU has increased by 41.86%

Figure 3:
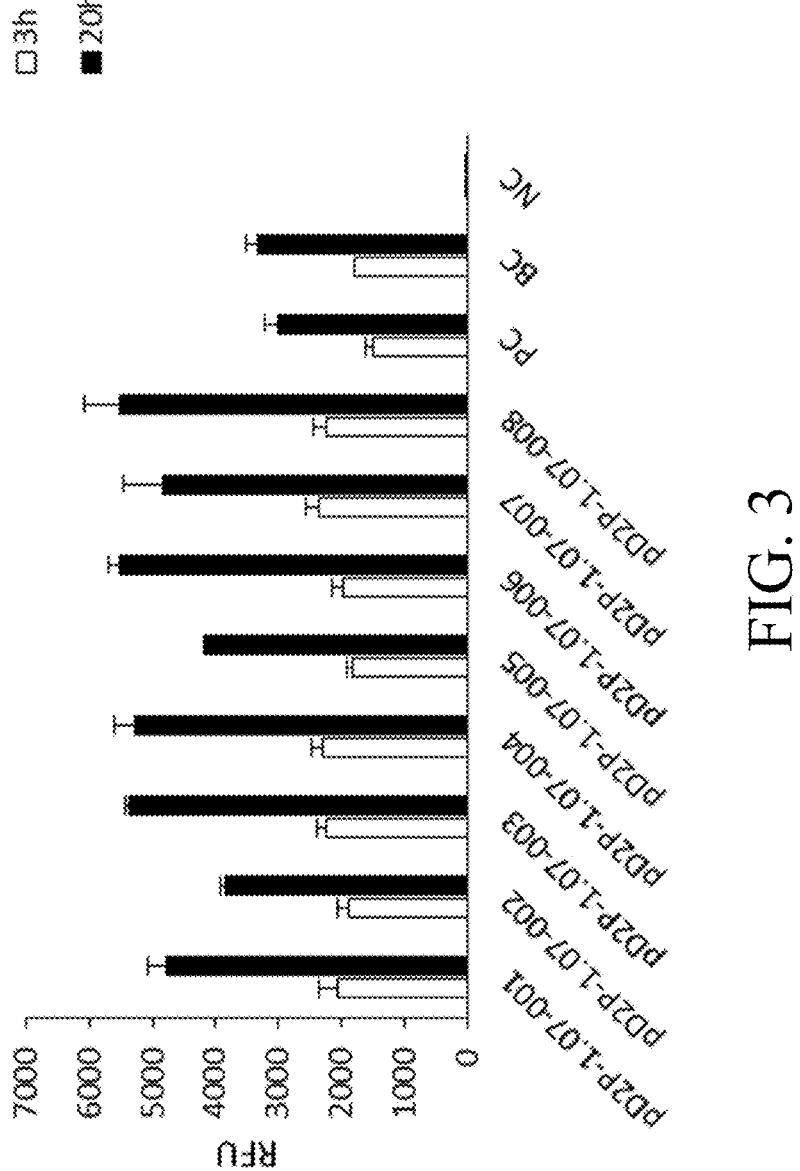

From Embodiment 4, it can be seen that, different experimental groups have all exceeded the blank control group, referencing to FIG. 3, wherein four experimental groups comprising the pD2P-1.07-003, pD2P-1.07-004, pD2P-1.07-006 and pD2P-1.07-008 have an effect significant, in particular, the PFU value of the pD2P-1.07-008 has reached 5532 after a 20-hour-reaction, comparing to a blank control (the RFU value is 3334) without any polypeptide tag correlation sequence inserted, the RFU value has increased by 65.93%.

Figure 4:
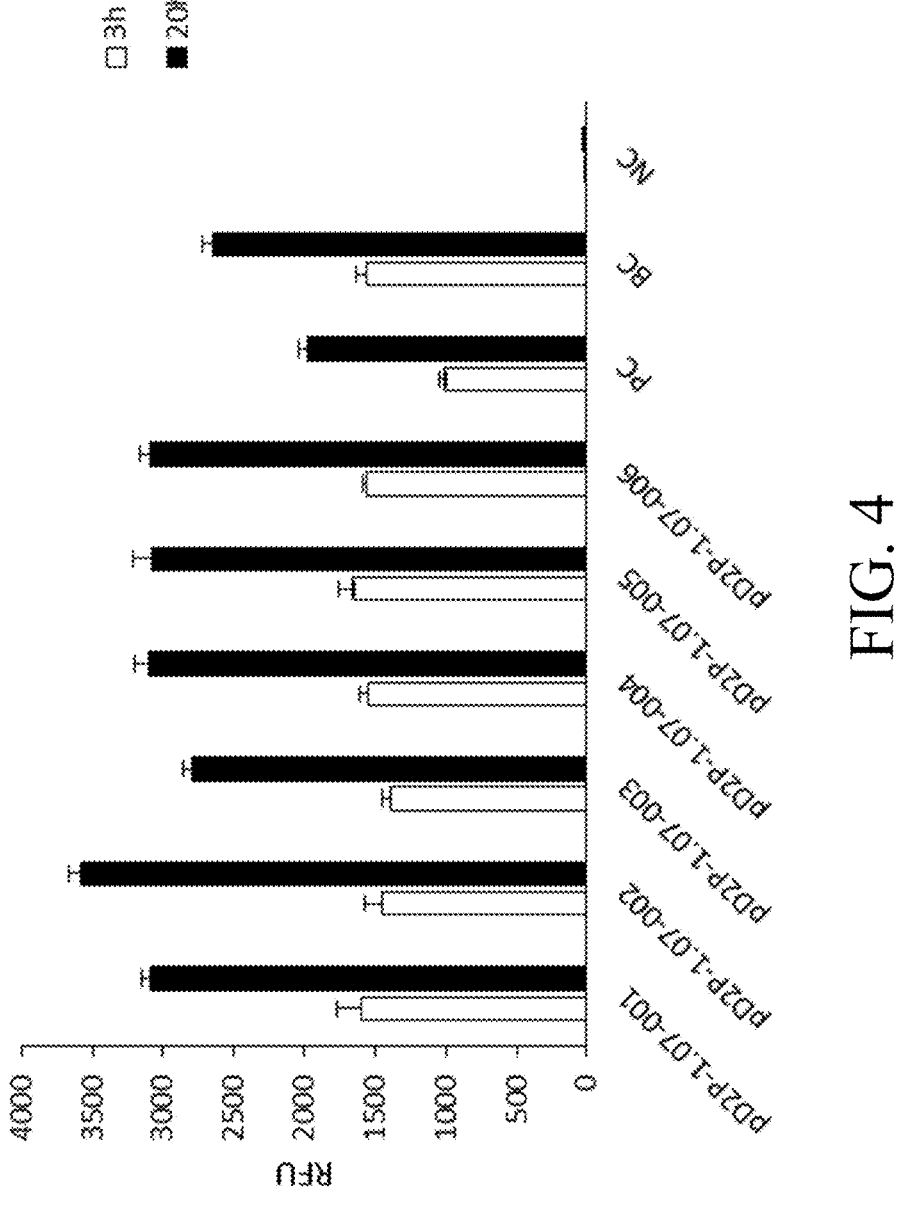

For the Embodiment 5, the different experimental groups have all exceeded the blank control group, referring to FIG. 4, after a 20-hour-reaction, the RFU value of the experimental group pD2P1-1.07-002 measured is 3580, comparing to a blank control without a sequence related to the polypeptide tag inserted, the RFU value is 2654, and the RFU of the experimental group has increased by 34.89%.

The experimental results of the embodiments mentioned above shows that, by introducing the polypeptide tag of the present application, in particular the polypeptide tag sequence fused to the N-terminus of the target protein, and adopting the in vitro cell-free protein synthesis system to synthesize the polypeptide fusion protein being constructed, the translation efficiency and the yield of the target protein will be improved, and an availability of the in-vitro protein synthesis system is greatly improved.

All documents mentioned herein are incorporated by reference in the present application as if each document were incorporated by reference individually. It should be understood that, the application of the present application is not limited to the above examples listed. Ordinary technical personnel in this field can improve or change the applications according to the above descriptions, all of these improvements and transforms should belong to the scope of protection in the appended claims of the present application.

REFERENCE

1. Garcia R A, Riley M R. Applied biochemistry and biotechnology. Humana Press; 1981.263-264p.
2. Fromm H J, Hargrove M. Essentials of Biochemistry. 2012;
3. Katzen F, Chang G, Kudlicki W. The past, present and future of cell-free protein synthesis. Trends Biotechnol. 2005; 23(3):150-6.
4. Gan R, Jewett M C. A combined cell-free transcription-translation system from *Saccharomyces cerevisiae* for rapid and robust protein synthesis. Biotechnol J. 2014; 9(5): 641-51.

5. Lu Y. Cell-free synthetic biology: Engineering in an open world. Synth Syst Biotechnol. 2017; 2(1):23-7.
6. Esposito D, Chatterjee D K Enhancement of soluble protein ex-pression through the use of fusion tags. Curr Opin Biotechnol. 2006; 17(4):353-358.
7. Kapust R B, Waugh D S *Escherichia coli* maltose-binding protein is uncommonly effective at promoting the solubility of polypeptides to which it is fused. Protein Science. 1999; 8(8):1668-1674.
8. Liangfan Zhou, Zhihui Zhao, Baocun Li, Yufeng Cai, Shuangquan Zhang. TrxA mediating fusion expression of antimicrobial peptide CM4 from multiple joined genes in *Escherichia coli*.Protein Expression and Puri-fication. 2009; 64(2):225-230.
9. Kohl T, Schmidt C, Wiemann S, Poustka A, Korf U Automated production of recombinant human proteins as resource for proteome research. Proteome Science. 2008; 6:4.
10. Hu J, Qin H, Sharma M, Cross T A, Gao F P Chemical cleavage of fusion proteins for high-level production of transmembrane peptides and protein domains contain-ing conserved methionines. Biochim Biophys Acta. 2008; 1778(4):1060-1066.
11. Da Sol Kim, Seon Woong Kim, Jae Min Song, Soon Young Kim&Kwang-Chul Kwon. A new prokaryotic expression vector for the expression of antimicrobial peptide abaecin using SUMO fusion tag. BMC Bio-technology. 2019; 19:13.
12. Thi Khoa My Nguyen, Mi Ran Ki, Ryeo Gang Son, Seung Pil Pack1. The NT11, a novel fusion tag for enhancing protein expression in *Escherichia coli*. Applied Microbiology and Biotechnology. 2019; 103 (5):2205-2216.

What is claimed is:

1. An isolated polypeptide tag mutant selected from the group consisting of SEQ ID NOs: 10-17.

2. A polypeptide fusion protein comprising: (1) the isolated polypeptide tag mutant according to claims 1, and (2) a target protein connected to the isolated polypeptide tag mutant.

3. The polypeptide fusion protein according to claim 2, wherein a C-terminus of the isolated polypeptide tag mutant is connected to an N-terminus of the target protein.

4. The polypeptide fusion protein according to claim 2, wherein the target protein is selected from the group consisting of: a fluorescent protein, an enhanced fluorescent protein, and a firefly luciferase; or a combination thereof.

5. An in vitro cell-free protein synthesis system, comprising:
(1) a cell extract;
(2) a DNA or an mRNA encoding the polypeptide fusion protein according to claim 2.

6. The in vitro cell-free protein synthesis system according to claim 5, wherein the cell extract is a yeast cell extract.

7. The in vitro cell-free protein synthesis system according to claim 5, further comprising one or more components selected from the group consisting of: an amino acid mixture, a dNTP, and an RNA polymerase.

8. The in vitro cell-free protein synthesis system according to claim 5, further comprising one or more components selected from the group consisting of: a DNA polymerase, an energy supply system, a polyethylene glycol, and an aqueous solvent.

9. The in vitro cell-free protein synthesis system according to claim 6, wherein the cell extract is a *Kluyveromyces lactis* yeast cell extract.

* * * * *

SEQUENCE LISTING

```
<160> NUMBER OF SEQ ID NOS: 38

<210> SEQ ID NO 1
<211> LENGTH: 33
<212> TYPE: DNA
<213> ORGANISM: Artificial Sequence
<220> FEATURE:
<223> OTHER INFORMATION: synthetic DNA {nucleotide sequence encoding a
      NT11 tag variant}

<400> SEQUENCE: 1
gtttctgaac cgcacgacta caactacgaa ccc                                    33

<210> SEQ ID NO 2
<211> LENGTH: 33
<212> TYPE: DNA
<213> ORGANISM: Artificial Sequence
<220> FEATURE:
<223> OTHER INFORMATION: synthetic DNA {nucleotide sequence encoding a
      NT11 tag variant}

<400> SEQUENCE: 2
gtttctgaac cgcacgacta caactacggg aaa                                    33

<210> SEQ ID NO 3
<211> LENGTH: 30
<212> TYPE: DNA
<213> ORGANISM: Artificial Sequence
<220> FEATURE:
<223> OTHER INFORMATION: synthetic DNA {nucleotide sequence encoding a
      NT11 tag variant}
```

-continued

```
<400> SEQUENCE: 3
tctgaaccgc acgactacaa ctacgaaaaa                                          30

<210> SEQ ID NO 4
<211> LENGTH: 30
<212> TYPE: DNA
<213> ORGANISM: Artificial Sequence
<220> FEATURE:
<223> OTHER INFORMATION: synthetic DNA {nucleotide sequence encoding a
      NT11 tag variant}

<400> SEQUENCE: 4
gtttctgaac cgcacgacta caactacgaa                                          30

<210> SEQ ID NO 5
<211> LENGTH: 27
<212> TYPE: DNA
<213> ORGANISM: Artificial Sequence
<220> FEATURE:
<223> OTHER INFORMATION: synthetic DNA {nucleotide sequence encoding a
      NT11 tag variant}

<400> SEQUENCE: 5
gaaccgcacg actacaacta cgaaaaa                                             27

<210> SEQ ID NO 6
<211> LENGTH: 27
<212> TYPE: DNA
<213> ORGANISM: Artificial Sequence
<220> FEATURE:
<223> OTHER INFORMATION: synthetic DNA {nucleotide sequence encoding a
      NT11 tag variant}

<400> SEQUENCE: 6
gtttctgaac cgcacgacta caactac                                            27

<210> SEQ ID NO 7
<211> LENGTH: 24
<212> TYPE: DNA
<213> ORGANISM: Artificial Sequence
<220> FEATURE:
<223> OTHER INFORMATION: synthetic DNA {nucleotide sequence encoding a
      NT11 tag variant}

<400> SEQUENCE: 7
ccgcacgact acaactacga aaaa                                               24

<210> SEQ ID NO 8
<211> LENGTH: 24
<212> TYPE: DNA
<213> ORGANISM: Artificial Sequence
<220> FEATURE:
<223> OTHER INFORMATION: synthetic DNA {nucleotide sequence encoding a
      NT11 tag variant}

<400> SEQUENCE: 8
gtttctgaac cgcacgacta caac                                               24

<210> SEQ ID NO 9
<211> LENGTH: 33
<212> TYPE: DNA
<213> ORGANISM: Artificial Sequence
<220> FEATURE:
<223> OTHER INFORMATION: synthetic DNA {nucleotide encoding NT11 tag,
      that is the first 11 amino acid residues within the N-terminal
      N-half domain of a duplicated carbonic anhydrase from Dunaliella
      species}
```

-continued

<400> SEQUENCE: 9
gtttctgaac cgcacgacta caactacgaa aaa                                              33

<210> SEQ ID NO 10
<211> LENGTH: 11
<212> TYPE: PRT
<213> ORGANISM: Artificial Sequence
<220> FEATURE:
<223> OTHER INFORMATION: synthetic peptide {variant of NT11 tag}

<400> SEQUENCE: 10

Val Ser Glu Pro His Asp Tyr Asn Tyr Glu Pro
1               5                   10

<210> SEQ ID NO 11
<211> LENGTH: 11
<212> TYPE: PRT
<213> ORGANISM: Artificial Sequence
<220> FEATURE:
<223> OTHER INFORMATION: synthetic peptide {variant of NT11 tag}

<400> SEQUENCE: 11

Val Ser Glu Pro His Asp Tyr Asn Tyr Gly Lys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: synthetic peptide {variant of NT11 tag}

<400> SEQUENCE: 12

Ser Glu Pro His Asp Tyr Asn Tyr Glu Lys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: synthetic peptide {variant of NT11 tag}

<400> SEQUENCE: 13

Val Ser Glu Pro His Asp Tyr Asn Tyr Glu
1               5                   10

<210> SEQ ID NO 14
<211> LENGTH: 9
<212> TYPE: PRT
<213> ORGANISM: Artificial Sequence
<220> FEATURE:
<223> OTHER INFORMATION: synthetic peptide {variant of NT11 tag}

<400> SEQUENCE: 14

Glu Pro His Asp Tyr Asn Tyr Glu Lys
1               5

<210> SEQ ID NO 15
<211> LENGTH: 9
<212> TYPE: PRT
<213> ORGANISM: Artificial Sequence
<220> FEATURE:
<223> OTHER INFORMATION: synthetic peptide {variant of NT11 tag}

<400> SEQUENCE: 15

-continued

```
Val Ser Glu Pro His Asp Tyr Asn Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic peptide {variant of NT11 tag}

<400> SEQUENCE: 16

Pro His Asp Tyr Asn Tyr Glu Lys
1               5

<210> SEQ ID NO 17
<211> LENGTH: 8
<212> TYPE: PRT
<213> ORGANISM: Artificial Sequence
<220> FEATURE:
<223> OTHER INFORMATION: synthetic peptide {variant of NT11 tag}

<400> SEQUENCE: 17

Val Ser Glu Pro His Asp Tyr Asn
1               5

<210> SEQ ID NO 18
<211> LENGTH: 11
<212> TYPE: PRT
<213> ORGANISM: Artificial Sequence
<220> FEATURE:
<223> OTHER INFORMATION: (Dunaliella)

<400> SEQUENCE: 18

Val Ser Glu Pro His Asp Tyr Asn Tyr Glu Lys
1               5                   10

<210> SEQ ID NO 19
<211> LENGTH: 42
<212> TYPE: DNA
<213> ORGANISM: Artificial Sequence
<220> FEATURE:
<223> OTHER INFORMATION: synthetic DNA {D2P-1.07-001_PF forward primer}

<400> SEQUENCE: 19
ccgcacgact acaactacga acccgtgagc aaggggggagg ag                         42

<210> SEQ ID NO 20
<211> LENGTH: 49
<212> TYPE: DNA
<213> ORGANISM: Artificial Sequence
<220> FEATURE:
<223> OTHER INFORMATION: synthetic DNA {D2P-1.07-001_PR reverse primer}

<400> SEQUENCE: 20
gggttcgtag ttgtagtcgt gcggttcaga aactttccca ctgtgggag                   49

<210> SEQ ID NO 21
<211> LENGTH: 42
<212> TYPE: DNA
<213> ORGANISM: Artificial Sequence
<220> FEATURE:
<223> OTHER INFORMATION: synthetic DNA {D2P-1.07-002_PF forward primer}

<400> SEQUENCE: 21
ccgcacgact acaactacgg gaaagtgagc aagggcgagg ag                          42
```

-continued

```
<210> SEQ ID NO 22
<211> LENGTH: 49
<212> TYPE: DNA
<213> ORGANISM: Artificial Sequence
<220> FEATURE:
<223> OTHER INFORMATION: synthetic DNA {D2P-1.07-002_PR reverse primer}

<400> SEQUENCE: 22
tttcccgtag ttgtagtcgt gcggttcaga aactttccca ctgtgggag              49

<210> SEQ ID NO 23
<211> LENGTH: 51
<212> TYPE: DNA
<213> ORGANISM: Artificial Sequence
<220> FEATURE:
<223> OTHER INFORMATION: synthetic DNA {D2P-1.07-003_PF forward primer}

<400> SEQUENCE: 23
tcccacagtg ggaaatctga accgcacgac tacaactacg aaaaagtgag c           51

<210> SEQ ID NO 24
<211> LENGTH: 56
<212> TYPE: DNA
<213> ORGANISM: Artificial Sequence
<220> FEATURE:
<223> OTHER INFORMATION: synthetic DNA {D2P-1.07-003_PR reverse primer}

<400> SEQUENCE: 24
cggttcagat ttcccactgt gggagaatat agatctgaac ggtgatgatg tttctg      56

<210> SEQ ID NO 25
<211> LENGTH: 42
<212> TYPE: DNA
<213> ORGANISM: Artificial Sequence
<220> FEATURE:
<223> OTHER INFORMATION: synthetic DNA {D2P-1.07-004_PF forward primer}

<400> SEQUENCE: 25
aactacgaag tgagcaaggg cgaggagctg ttcaccgggg tg                     42

<210> SEQ ID NO 26
<211> LENGTH: 46
<212> TYPE: DNA
<213> ORGANISM: Artificial Sequence
<220> FEATURE:
<223> OTHER INFORMATION: synthetic DNA {D2P-1.07-004_PR reverse primer}

<400> SEQUENCE: 26
ctcgcccttg ctcacttcgt agttgtagtc gtgcggttca gaaact                 46

<210> SEQ ID NO 27
<211> LENGTH: 49
<212> TYPE: DNA
<213> ORGANISM: Artificial Sequence
<220> FEATURE:
<223> OTHER INFORMATION: synthetic DNA {D2P-1.07-005_PF forward primer}

<400> SEQUENCE: 27
acagtgggaa agaaccgcac gactacaact acgaaaaagt gagcaaggg              49

<210> SEQ ID NO 28
<211> LENGTH: 51
<212> TYPE: DNA
<213> ORGANISM: Artificial Sequence
<220> FEATURE:
<223> OTHER INFORMATION: synthetic DNA {D2P-1.07-005_PR reverse primer}
```

-continued

<400> SEQUENCE: 28
agtcgtgcgg ttctttccca ctgtgggaga atatagatct gaacggtgat g          51

<210> SEQ ID NO 29
<211> LENGTH: 42
<212> TYPE: DNA
<213> ORGANISM: Artificial Sequence
<220> FEATURE:
<223> OTHER INFORMATION: synthetic DNA {D2P-1.07-006_PF forward primer}

<400> SEQUENCE: 29
tctgaaccgc acgactacaa ctacgtgagc aagggcgagg ag                     42

<210> SEQ ID NO 30
<211> LENGTH: 51
<212> TYPE: DNA
<213> ORGANISM: Artificial Sequence
<220> FEATURE:
<223> OTHER INFORMATION: synthetic DNA {D2P-1.07-006_PR reverse primer}

<400> SEQUENCE: 30
gtagttgtag tcgtgcggtt cagaaacttt cccactgtgg gagaatatag a          51

<210> SEQ ID NO 31
<211> LENGTH: 48
<212> TYPE: DNA
<213> ORGANISM: Artificial Sequence
<220> FEATURE:
<223> OTHER INFORMATION: synthetic DNA {D2P-1.07-007_PF forward primer}

<400> SEQUENCE: 31
agtgggaaac cgcacgacta caactacgaa aaagtgagca aggggcga              48

<210> SEQ ID NO 32
<211> LENGTH: 51
<212> TYPE: DNA
<213> ORGANISM: Artificial Sequence
<220> FEATURE:
<223> OTHER INFORMATION: synthetic DNA {D2P-1.07-007_PR reverse primer}

<400> SEQUENCE: 32
gttgtagtcg tgcggtttcc cactgtggga gaatatagat ctgaacggtg a          51

<210> SEQ ID NO 33
<211> LENGTH: 42
<212> TYPE: DNA
<213> ORGANISM: Artificial Sequence
<220> FEATURE:
<223> OTHER INFORMATION: synthetic DNA {D2P-1.07-008_PF forward primer}

<400> SEQUENCE: 33
gtttctgaac cgcacgacta caacgtgagc aagggcgagg ag                     42

<210> SEQ ID NO 34
<211> LENGTH: 52
<212> TYPE: DNA
<213> ORGANISM: Artificial Sequence
<220> FEATURE:
<223> OTHER INFORMATION: synthetic DNA {D2P-1.07-008_PR reverse primer}

<400> SEQUENCE: 34
gttgtagtcg tgcggttcag aaactttccc actgtgggag aatatagatc tg         52

<210> SEQ ID NO 35

```
<211> LENGTH: 46
<212> TYPE: DNA
<213> ORGANISM: Artificial Sequence
<220> FEATURE:
<223> OTHER INFORMATION: synthetic DNA {PC_PF forward primer}

<400> SEQUENCE: 35
gtttctgaac cgcacgacta caactacgaa aaagtgagca agggcg                    46

<210> SEQ ID NO 36
<211> LENGTH: 55
<212> TYPE: DNA
<213> ORGANISM: Artificial Sequence
<220> FEATURE:
<223> OTHER INFORMATION: synthetic DNA {PC_PR reverse primer}

<400> SEQUENCE: 36
gttgtagtcg tgcggttcag aaactttccc actgtgggag aatatagatc tgaac         55

<210> SEQ ID NO 37
<211> LENGTH: 11
<212> TYPE: PRT
<213> ORGANISM: Artificial Sequence
<220> FEATURE:
<223> OTHER INFORMATION: synthetic peptide {the polypeptide tag}
<220> FEATURE:
<221> NAME/KEY: MISC_FEATURE
<222> LOCATION: (1)..(1)
<223> OTHER INFORMATION: The Xaa is the Xaa1,  the Xaa1 in the amino
      acid sequence of the polypeptide tag is V or none
<220> FEATURE:
<221> NAME/KEY: MISC_FEATURE
<222> LOCATION: (2)..(2)
<223> OTHER INFORMATION: The Xaa is the Xaa2, the Xaa2 in the amino acid
      sequence of the polypeptide tag is S or none
<220> FEATURE:
<221> NAME/KEY: MISC_FEATURE
<222> LOCATION: (3)..(3)
<223> OTHER INFORMATION: The Xaa is the Xaa3, the Xaa3 in the amino acid
      sequence of the polypeptide tag is E or none
<220> FEATURE:
<221> NAME/KEY: MISC_FEATURE
<222> LOCATION: (9)..(9)
<223> OTHER INFORMATION: The Xaa is the Xaa4, the Xaa4 in the amino acid
      sequence of the polypeptide tag is Y or none
<220> FEATURE:
<221> NAME/KEY: MISC_FEATURE
<222> LOCATION: (10)..(10)
<223> OTHER INFORMATION: The Xaa is the Xaa5, the Xaa5 in the amino acid
      sequence of the polypeptide tag is E or G or none
<220> FEATURE:
<221> NAME/KEY: MISC_FEATURE
<222> LOCATION: (11)..(11)
<223> OTHER INFORMATION: The Xaa is the Xaa6, the Xaa6 in the amino acid
      sequence of the polypeptide tag is P or K or none

<400> SEQUENCE: 37

Xaa Xaa Xaa Pro His Asp Tyr Asn Xaa Xaa Xaa
1               5                   10

<210> SEQ ID NO 38
<211> LENGTH: 7
<212> TYPE: DNA
<213> ORGANISM: Artificial Sequence
<220> FEATURE:
<223> OTHER INFORMATION: random primer
```

-continued

```
<220> FEATURE:
<221> NAME/KEY: misc_feature
<222> LOCATION: (1)..(7)
<223> OTHER INFORMATION: n is a, c, g, or t

<400> SEQUENCE: 38 nnnnnnn                                                              7
```